(12) United States Patent
Brown et al.

(10) Patent No.: US 7,737,314 B2
(45) Date of Patent: Jun. 15, 2010

(54) PRODUCTION OF HIGH PURITY ETHYLBENZENE FROM NON-EXTRACTED FEED AND NON-EXTRACTED REFORMATE USEFUL THEREIN

(75) Inventors: Stephen H. Brown, Bernardsville, NJ (US); Nick A. Collins, Fall Branch, TN (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 794 days.

(21) Appl. No.: 11/705,278

(22) Filed: Feb. 12, 2007

(65) Prior Publication Data

US 2008/0194896 A1 Aug. 14, 2008

(51) Int. Cl.
C07C 2/58 (2006.01)

(52) U.S. Cl. .................. 585/467; 585/448

(58) Field of Classification Search .......... 585/448, 585/467
See application file for complete search history.

(56) References Cited

U.S. PATENT DOCUMENTS

| | | | |
|---|---|---|---|
| 4,291,185 A | 9/1981 | Kaeding | |
| 5,149,894 A | 9/1992 | Holtermann et al. | |
| 5,221,777 A | 6/1993 | Huss, Jr. et al. | |
| 5,258,565 A * | 11/1993 | Kresge et al. | 585/467 |
| 5,258,569 A | 11/1993 | Chu et al. | |
| 5,273,644 A | 12/1993 | Wegerer | |
| 5,866,736 A | 2/1999 | Chen | |
| 5,894,076 A | 4/1999 | Hearn et al. | |
| 6,002,058 A | 12/1999 | Hearn et al. | |
| 6,313,362 B1 | 11/2001 | Green et al. | |
| 6,339,179 B1 | 1/2002 | Schulz et al. | |
| 6,355,851 B1 | 3/2002 | Wu et al. | |

2006/0247479 A1 11/2006 Barchha et al.

FOREIGN PATENT DOCUMENTS

| | | |
|---|---|---|
| AU | 9338931 | 11/1993 |
| AU | 9865738 | 12/1998 |
| CA | 2133305 | 3/1999 |
| CN | 1042221 | 1/1995 |
| CN | 1097187 | 1/1995 |
| DE | 69304687 | 10/1996 |
| EP | 633 872 | 1/1995 |
| EP | 988 264 | 3/2000 |
| EP | 1 369 465 | 12/2003 |
| ES | 2092294 | 11/1996 |
| FR | 2689501 | 10/1993 |
| JP | 2535321 | 2/1995 |
| JP | 1996511514 A | 12/1996 |
| JP | 2001525007 | 12/2001 |
| JP | 200281595 | 3/2002 |
| KR | 146023 | 8/1998 |
| KR | 2001012449 | 2/2001 |
| MX | 9 910 359 | 4/2000 |
| MX | 208771 | 7/2002 |
| RU | 2114810 | 7/1998 |
| WO | WO 98/20029 | 5/1998 |
| WO | WO 98/51648 | 11/1998 |
| WO | WO 2006/032400 | 3/2006 |

* cited by examiner

*Primary Examiner*—Thuan Dinh Dang
(74) *Attorney, Agent, or Firm*—D. M. Tyus

(57) ABSTRACT

A process for producing an ethylbenzene product having a purity of at least 99.50 percent based on the weight of ethylbenzene present in the product by the ethylation of the benzene present in non-extracted feed, e.g., non-extracted hydrocarbon composition. The non-extracted feed is substantially free of both $C_4-$ hydrocarbons and the $C_7+$ aromatic hydrocarbons and contains benzene and benzene coboilers. The process is carried out in the liquid phase, in the presence of an acid-active catalyst containing MCM-22 family molecular sieve, and under specified conditions.

11 Claims, 5 Drawing Sheets

PRODUCTION OF HIGH PURITY ETHYLBENZENE FROM NON-EXTRACTED FEED AND NON-EXTRACTED REFORMATE USEFUL THEREIN

FIELD OF THE INVENTION

This disclosure relates to a process for producing high purity ethylbenzene by the ethylation of benzene present in non-extracted hydrocarbon composition feed.

BACKGROUND OF THE INVENTION

Ethylbenzene, $C_8H_{10}$, is a key raw material in the production of styrene and is produced by the ethylation reaction of ethylene, $C_2H_4$, and benzene, $C_6H_6$, in a catalytic environment. When sold as a commodity product, the product will usually contain at least 99.95 weight percent of ethylbenzene based on the weight of the product.

A source of benzene is reformate, which is prepared by contacting a mixture of petroleum naphtha and hydrogen with a reforming catalyst containing a support, e.g., halogen-treated alumina or non-acidic zeolite L, and a hydrogenation/dehydrogenation metal, e.g., Group 8, 9, or 10 metal such as platinum. That process typically produces a reformate that includes $C_5$- hydrocarbons, $C_6$-$C_8$ aromatic hydrocarbons, e.g., benzene, $C_9$+ hydrocarbons, $C_6$+ paraffins, and cyclo-paraffins (naphthenes).

Another source of benzene is the cracking of hydrocarbons such as by steam cracking or catalytic cracking. That process typically produces an effluent that includes $C_6$-$C_8$ aromatic hydrocarbons, e.g., benzene, $C_6$+ paraffins, and naphthenes.

Still another source for producing aromatics is the dehydrocyclo-oligomerization of $C_2$-$C_5$ aliphatic hydrocarbons. That process typically produces a product effluent that includes $C_6$-$C_8$ aromatic hydrocarbons, e.g., benzene, $C_6$+ paraffins, naphthenes and $C_5$ aliphatic hydrocarbons.

Benzene can be separated from other reformate hydrocarbons, e.g., $C_7$+ aromatics, by distillation. However, the benzene obtained by distillation will usually contain $C_6$ and $C_7$ non-aromatic hydrocarbon impurities that are difficult to separate from benzene by distillation because they have boiling points close to the boiling point of benzene, i.e., their boiling point is within 10° C. of benzene (boiling point of 80.1° C.) at a pressure of about 101.3 kPa-a (absolute). This feed may also contain $C_5$ paraffins and naphthenes, such as n-pentane and cyclopentane. These impurities, which are hereinafter sometimes referred to as "benzene coboilers", may be present in the distillate product in an amount up to 75 percent by weight based on the weight of the product. Examples of benzene coboilers include cyclohexane, methylcyclopentane, 2-methylhexane, 3-methylhexane, 2,3-dimethylpentane, 2,4-dimethylpentane, and dimethylcyclopentane.

The presence of these impurities during the ethylation of benzene can result in an ethylbenzene product having less than desirable purity. For example, the presence of benzene coboilers during the ethylation of benzene can result in the formation of ethylbenzene coboilers (hydrocarbons having a boiling point within 10° C. of the boiling point of ethylbenzene [boiling point of 136° C.] at a pressure of about 1 atm) that can not be easily removed from the ethylbenzene product by distillation. It is well known, e.g., disclosed in U.S. Pat. Nos. 5,258,569 and 5,221,777, that ethylbenzene coboilers can be formed by isoparaffin/olefin alkylation reactions.

Because of the deleterious effect of benzene coboilers, benzene obtained by distillation usually undergoes an additional step, i.e., extraction such as liquid extraction or extractive distillation, to remove benzene coboilers from the benzene product before the benzene is ethylated to form ethylbenzene. Generally, benzene used in the ethylation of benzene to produce high purity ethylbenzene has a purity of about at least 99.985 weight percent by weight based on the weight of benzene present in the benzene distillate. However, the extraction step is expensive and time consuming, which results in increased costs in manufacture of high purity ethylbenzene.

By the present disclosure, a process is provided for ethylation of benzene to produce high purity ethylbenzene that uses feed containing benzene that has not undergone extraction.

SUMMARY OF THE INVENTION

The present disclosure is directed to a process for producing an ethylbenzene product having a purity of at least 99.50 percent based on the weight of ethylbenzene present in the product using a hydrocarbon composition feed that has not undergone extraction. The non-extracted hydrocarbon composition feed is substantially free of $C_4$- hydrocarbons and $C_7$+ aromatic hydrocarbons, and contains benzene and from about 1 to about 75 percent, from about 2 to about 75 percent, from about 3 to about 75 percent, from about 5 to about 75 percent, or from about 10 to about 75 percent, by weight of at least one $C_6$+ non-aromatic hydrocarbon having a boiling point within 10° C. at a pressure of about 101.3 kPa-a of the boiling point of benzene. The phrase "substantially free of $C_4$- hydrocarbons and $C_7$+ aromatic hydrocarbons" means that the hydrocarbon composition feed contains less than about 0.05 percent by weight and, more preferably, less than about 0.01 percent by weight of $C_4$- hydrocarbons and $C_7$+ aromatic hydrocarbons based on the weight of the hydrocarbon composition feed. The process is carried out by: (a) alkylating the benzene with ethylene in at least partial liquid phase with an acid-active catalyst having an alpha value in a range from about 1 to about 1000 at conditions that include a temperature in the range of from about 162.8° C. to about 232.2° C., a pressure sufficient to maintain the benzene in the liquid phase, usually at least 689.5 kPa-a, e.g., from about 689.5 kPa-a to about 6.89 MPa-a, a mole ratio of ethylene to benzene in the range of from about 0.001:1 to about 0.75:1, and a WHSV based on total ethylene over total catalyst for overall reactor in the range of from about 0.1 to about 10 hr$^{-1}$; and (b) distilling the product of step (a) to produce an ethylbenzene product having a purity of at least 99.50 percent based on the weight of ethylbenzene present in the product.

In another embodiment, the present disclosure is directed to a process for producing an ethylbenzene product having a purity of at least 99.50 percent based on the weight of ethylbenzene present in the product from a hydrocarbon composition that comprises: (i) $C_5$- hydrocarbons; (ii) benzene; (iii) $C_7$+ aromatic hydrocarbons; and (iv) from about 1 to about 75 percent by weight of at least one $C_6$+ non-aromatic hydrocarbon having a boiling point within 10° C. at a pressure of about 101.3 kPa-a of the boiling point of benzene. The process is carried out by: (a) removing $C_4$- hydrocarbons and the $C_7$+ aromatic hydrocarbons from the reformate by distillation to form the hydrocarbon composition; and (b) alkylating the benzene present in the hydrocarbon composition of step (a) (without extraction of said reformate) with ethylene in at least partial liquid phase with a catalyst comprising at least one of a crystalline MCM-22 family material and a zeolite beta molecular sieve at conditions that include a temperature in the range of from about 162.8° C. to about 232.2° C., a pressure sufficient to maintain the benzene in the liquid phase, usually at least 689.5 kPa-a, e.g., from about 689.5 kPa-a to about 6.89 MPa-a, a mole ratio of ethylene to benzene in the range of from about 0.001:1 to about 0.75:1, and a WHSV based on total ethylene over total catalyst for overall reactor in the range of from about 0.1 to about 10 hr$^{-1}$; (c) distilling the product of step (b) to produce an ethylbenzene product having a purity of at least 99.50 percent based on the weight of ethylbenzene present in the product

DETAILED DESCRIPTION OF THE DISCLOSURE

Figure 1:
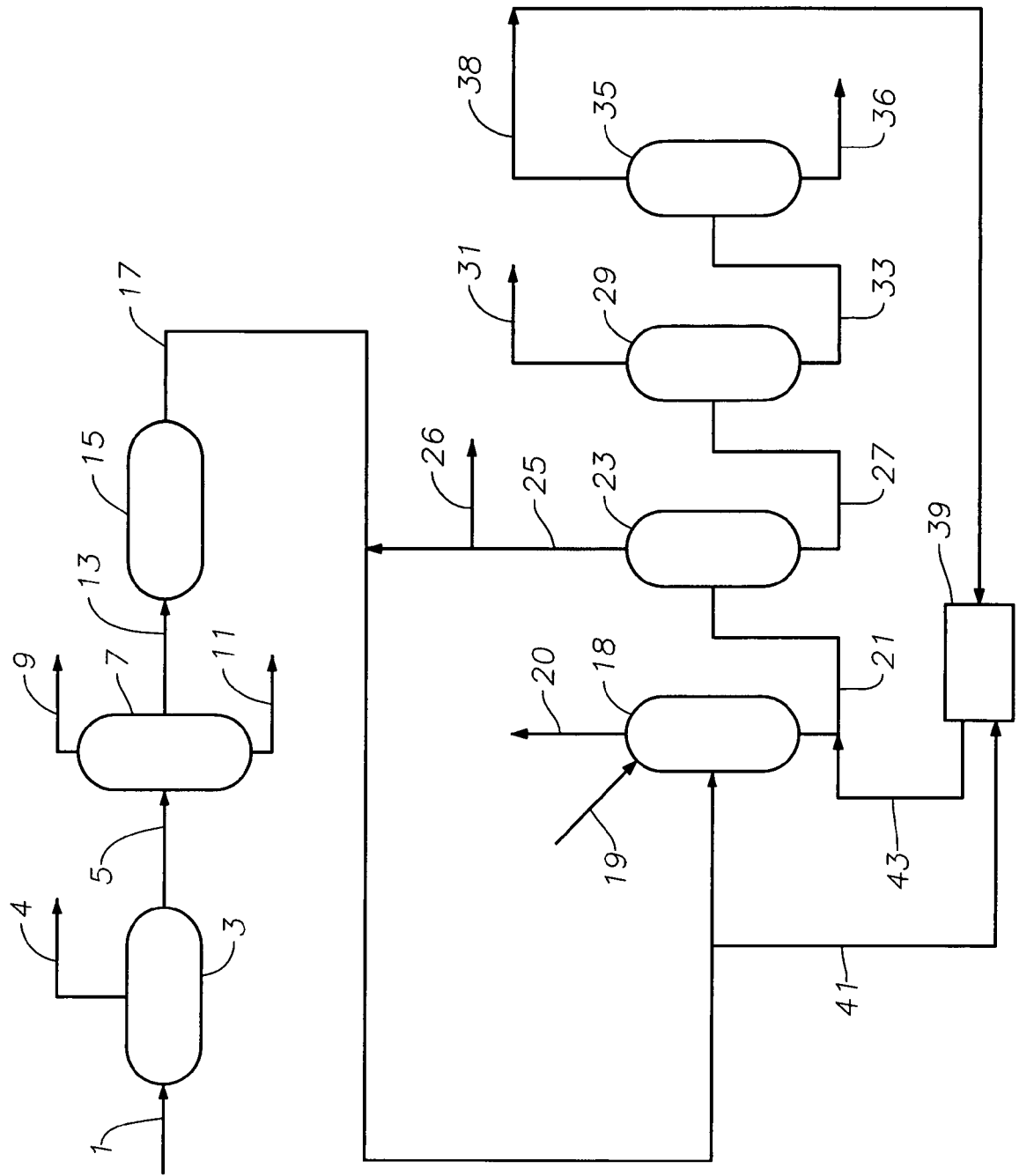
FIG. 1 is a simplified process flow diagram, illustrating an embodiment of the disclosure.

All patents, patent applications, test procedures, priority documents, articles, publications, manuals, and other documents cited herein are fully incorporated by reference to the extent such disclosure is not inconsistent with the present disclosure and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "aromatization", as used herein, shall mean the production of aromatics comprising benzene, toluene, or mixtures thereof by the conversion of non-aromatic hydrocarbons to aromatic hydrocarbons comprising benzene, toluene, or mixtures thereof. The term "aromatization", as used herein, shall also include the production of aromatics comprising benzene, toluene, or mixtures thereof by the cracking of heavy aromatic hydrocarbons to produce the aromatic hydrocarbons comprising benzene, toluene, or mixtures. Examples of aromatization processes include catalytic reforming of naphtha, dehydrocyclo-oligomerization of $C_2$-$C_5$ aliphatic hydrocarbons, steam cracking of hydrocarbons to produce aromatic hydrocarbons comprising benzene, toluene, or mixtures thereof, and the catalytic cracking of hydrocarbons to produce aromatic hydrocarbons comprising benzene, toluene, or mixtures thereof.

The term "reformate", as used herein, shall mean the product produced by "aromatization".

The term "$C_n$" hydrocarbon wherein n is an positive integer, e.g., 1, 2, 3, 4, 5, 6, 7, 8, 9, 10, 11, 12, as used herein means a hydrocarbon having n number of carbon atom(s) per molecular. For example, $C_n$ aromatics means an aromatic hydrocarbon having n number of carbon atom(s) per molecular; $C_n$ paraffin means a paraffin hydrocarbon having n number of carbon atom(s) per molecular; $C_n$ olefin means an olefin hydrocarbon having n number of carbon atom(s) per molecular. The term "$C_n$+" hydrocarbon wherein n is an positive integer, e.g., 1, 2, 3, 4, 5, 6, 7, 8, 9, 10, 11, 12, as used herein means a hydrocarbon having at least n number of carbon atom(s) per molecular. The term "$C_n$-" hydrocarbon wherein n is an positive integer, e.g., 1, 2, 3, 4, 5, 6, 7, 8, 9, 10, 11, 12, as used herein means a hydrocarbon having no more than n number of carbon atom(s) per molecular.

As used herein, an "alkylatable aromatic compound" is a compound that may receive an alkyl group and an "alkylating agent" is a compound which may donate an alkyl group to an alkylatable aromatic compound. One example of the alkylatable aromatic compounds is benzene. Examples of the alkylating agent are ethylene, propylene, polyalkylated aromatic compound(s), e.g., di-ethylbenzene, tri-ethylbenzene, di-isopropylbenzene, and tri-isopropylbenzene The term "wppm" as used herein is defined as parts per million by weight.

The term "at least partially in liquid phase" as used herein is understood as a mixture having at least 1 wt. % liquid phase, optionally at least 5 wt. % liquid phase at a given temperature, pressure, and composition.

The term "substantially in liquid phase" as used herein is understood as a mixture having at least 95 wt. % liquid phase, optionally at least 99 wt. % liquid phase at a given temperature, pressure, and composition.

The term "aromatic" as used herein is to be understood in accordance with its art-recognized scope which includes alkyl substituted and unsubstituted mono- and polynuclear compounds. Compounds of an aromatic character, which possess a heteroatom, are also useful provided sufficient activity can be achieved if they act as catalyst poisons under the reaction conditions selected.

The term "at least partially in liquid phase" as used herein is understood as a mixture having at least 1 wt. % liquid phase, optionally at least 5 wt. % liquid phase at a given temperature, pressure, and composition.

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697), and UZM-8 (described in U.S. Pat. No. 6,756,030). The entire contents of the patents are incorporated herein by reference.

It is to be appreciated the MCM-22 family molecular sieves described above are distinguished from conventional large pore zeolite alkylation catalysts, such as mordenite, in that the MCM-22 family materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly ethylbenzene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

An embodiment of the present disclosure is depicted in FIG. 1. Referring to FIG. 1, naphtha is introduced via line 1 into reactor zone 3 where the naphtha is reformed or steam cracked into aromatic products including benzene. Although only one reactor zone is shown, there can be more than one reactor zone. In reactor zone 3, $C_4-$ hydrocarbons are removed from the reformate via line 4 and the remaining reformate is withdrawn from reactor zone 3 via line 5 and introduced into column 7 where the feed is fractionated to form a light reformate fraction, a heavy reformate fraction, and a benzene/benzene coboiler fraction. The light reformate fraction is withdrawn from column 7 through line 9, the heavy reformate fraction is withdrawn from column 7 through line 11, and the benzene/benzene coboiler fraction is withdrawn from column 7 through line 13 and introduced into zone 15. In zone 15, catalyst poisons, e.g., sulfur, nitrogen, olefins, dienes, or combinations thereof are at least partially removed from the benzene/benzene coboiler fraction. The resulting fraction is withdrawn from zone 15 via line 17 and introduced into ethylation zone 18. In ethylation zone 18, ethylene is introduced via line 19 and benzene is reacted with the ethylene to form ethylbenzene. Low molecular weight molecules, such as ethylene and ethane, are withdrawn from ethylation zone 18 via line 20. The ethylbenzene-containing product is withdrawn from ethylation zone 18 via line 21 and introduced into column 23. In column 23, the ethylbenzene-containing product is fractionated to form a $C_7-$ fraction and a $C_8+$ fraction comprised of ethylbenzene and polyethylbenzenes. The $C_7-$ fraction is withdrawn from column 23 via line 25 and either removed from the unit via line 26 or recycled via line 17 to ethylation zone 18. The $C_8+$ fraction is withdrawn from column 23 via line 27 and introduced into column 29 via line 27. In Column 29, the $C_8+$ fraction is fractionated to form a high purity ethylbenzene product fraction and a $C_9+$ fraction comprised of polyethylbenzenes. The high purity ethylbenzene product fraction is withdrawn from column 29 via line 31 and recovered without the need for further purification. The ethylbenzene product will usually have a purity that exceeds 99.50 percent by weight based on the total weight of the product.

The remaining $C_9+$ fraction can undergo further processing. As exemplified in FIG. 1, $C_9+$ fraction is withdrawn from column 29 via line 33 and introduced into column 35. In column 35, polyethylbenzenes are separated from $C_{13}+$ hydrocarbons. The $C_{13}+$ hydrocarbon fraction is withdrawn from column 35 via line 36 and the polyethylbenzenes are withdrawn from column 35 via line 38 and introduced into transalkylation zone 39. In transalkylation zone 39, the polyethylbenzenes are transalkylated with benzene to form ethylbenzene. Benzene can be introduced into transalkylation zone 39 via line 41 or the benzene can be a fresh supply. The transalkylation product from transalkylation zone 39 is transferred to column 23 via lines 43 and 21 for processing.

Figure 2:
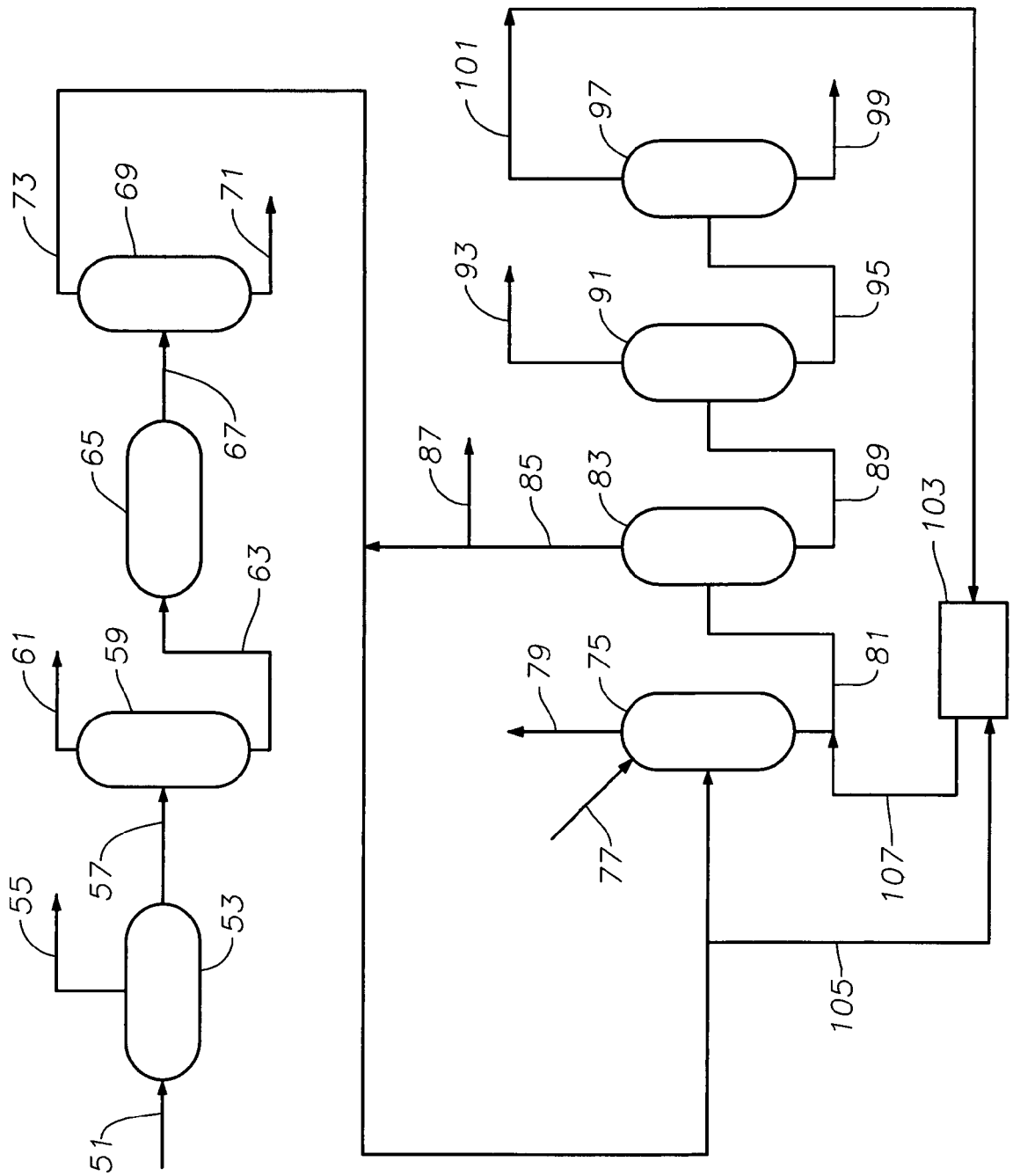
FIG. 2 is a simplified process flow diagram, illustrating another embodiment of the disclosure.

Another embodiment of the present disclosure is depicted in FIG. 2. Referring to FIG. 2, naphtha is introduced via line 51 into reactor zone 53 where the naphtha is reformed into aromatic products including benzene. Although only one reactor zone is shown, there can be more than one reactor zone. In reactor zone 53, $C_4-$ hydrocarbons are removed from the reformate via line 55 and the remaining reformate is withdrawn from reactor zone 53 via line 57 and introduced into column 59 where the feed is fractionated to form a light reformate fraction and a heavy reformate fraction. The light reformate fraction is withdrawn from column 59 through line 61 and the heavy reformate fraction containing benzene and benzene coboilers is withdrawn from column 59 through line 63, and introduced into zone 65. In zone 65, olefins, dienes, or combinations thereof are removed from the heavy reformate fraction. The resulting fraction is withdrawn from zone 65 via line 67 and introduced into column 69 where the feed is fractionated to form a benzene/benzene coboiler fraction and a $C_7+$ aromatic fraction. The $C_7+$ aromatic fraction is removed from column 69 fraction via line 71. The benzene/benzene coboiler fraction is withdrawn from column 69 via line 73 and introduced into ethylation zone 75. Ethylene is introduced into ethylation zone 75 via line 77 and benzene is reacted with the ethylene to form ethylbenzene. Low molecular weight molecules, such as ethylene and ethane, are withdrawn from ethylation zone 75 via line 79. The ethylbenzene-containing product is withdrawn from ethylation zone 75 via line 81 and introduced into column 83. In column 83, the ethylbenzene-containing product is fractionated to form a $C_7-$ fraction and a $C_8+$ fraction comprised of ethylbenzene and polyethylbenzenes. The $C_7-$ fraction is withdrawn from column 83 via line 85 and either removed from the unit via line 87 or recycled via line 73 to ethylation zone 75. The $C_8+$ fraction is withdrawn from column 83 via line 89 and introduced into column 91. In Column 91, the $C_8+$ fraction is fractionated and forms a high purity ethylbenzene product fraction and a $C_9+$ fraction comprised of polyethylbenzenes. The high purity ethylbenzene product fraction is withdrawn from column 91 via line 93 and recovered without the need for further purification. The ethylbenzene product will usually have a purity that exceeds 99.50 percent by weight based on the total weight of the product.

The remaining $C_9+$ fraction can undergo further processing. As exemplified in FIG. 2, $C_9+$ fraction is withdrawn from column 91 via line 95 and introduced into column 97. In column 97, polyethylbenzenes are separated from $C_{13}+$ hydrocarbons. The $C_{13}+$ hydrocarbon fraction is withdrawn from column 97 via line 99 and the polyethylbenzenes are withdrawn from column 97 via line 101 and transferred to transalkylation zone 103. In transalkylation zone 103, the polyethylbenzenes are reacted with benzene to form ethylbenzene. Benzene can be introduced into transalkylation zone 103 via line 105 or the benzene can be a fresh supply. The transalkylation product from transalkylation zone 103 is transferred to column 83 via lines 107 and 81 for processing.

Figure 3:
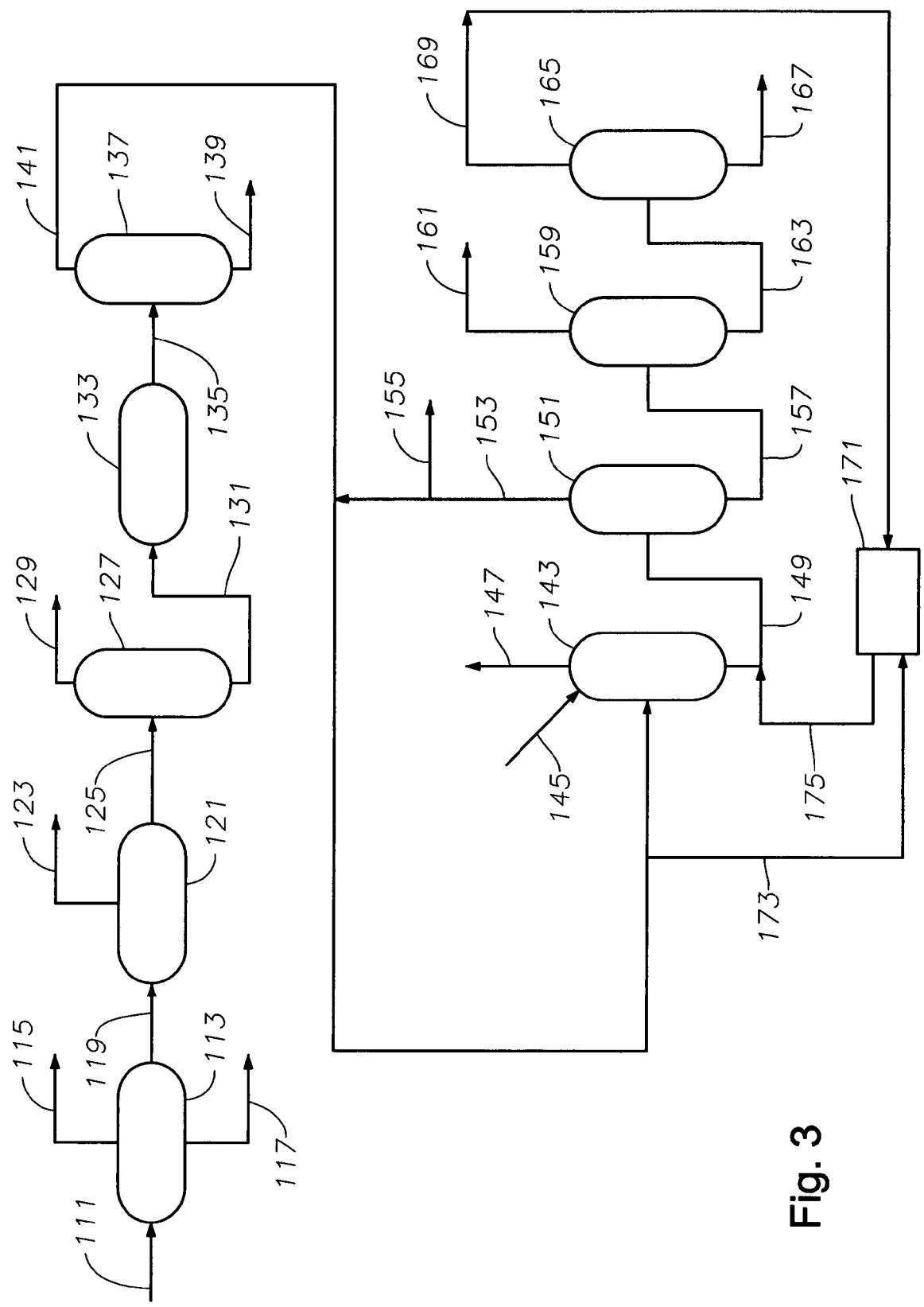
FIG. 3 is a simplified process flow diagram, illustrating a further embodiment of the disclosure.

A further embodiment of the present disclosure is depicted in FIG. 3. Referring to FIG. 3, naphtha having sufficient temperature is introduced via line 111 into reactor zone 113 where the naphtha undergoes steam cracking resulting in a product containing aromatics including benzene. Although only one reactor zone is shown, there can be more than one reactor zone. In reactor zone 113, $C_4-$ hydrocarbons are removed via line 115 and a heavy fraction is removed via line 117. The fraction containing benzene and benzene coboilers is withdrawn from reactor zone 113 via line 119 and introduced into zone 121 where the fraction is hydroprocessed to at least partially remove sulfur and nitrogen. Preferably, the fraction after treatment contains less than 5 wppm of sulfur and less than 1 wppm of nitrogen. $C_4-$ hydrocarbons are removed from zone 121 via line 123. The remaining fraction is removed from zone 121 via 125 and transferred to column 127 where the feed is fractionated to form a $C_5-$ hydrocarbon fraction and $C_6+$ hydrocarbon fraction. The $C_5-$ hydrocarbon fraction is withdrawn from column 127 via line 129. The $C_6+$ hydrocarbon fraction is withdrawn from column 127 via line 131 and introduced into zone 133 where the fraction is treated to at least partially remove dienes and olefins. After treatment, the fraction preferably contains less than 2500 wppm of olefins and dienes. After the treatments described above, the reformate will preferably be substantially free of $C_4-$ hydrocarbons and $C_7+$ aromatic hydrocarbons and contain benzene; from about 1 to about 75 percent by weight based on the weight of the reformate, of at least one $C_6+$ non-aromatic hydrocarbon having a boiling point within 10° C. at a pressure of about 101.3 kPa-a of the boiling point of benzene; less than 5 wppm of sulfur; less than 1 wppm of nitrogen; and less than 2500 wppm of olefins and dienes.

The fraction is then withdrawn from zone 133 via line 135 and introduced into column 137 where the feed is fractionated to form a fraction containing benzene and benzene coboilers and a $C_7+$ aromatic fraction. The $C_7+$ aromatic fraction is removed from column 137 via line 139. The benzene/benzene coboiler fraction is withdrawn from column 137 via line 141 and introduced into ethylation zone 143. Ethylene is introduced into ethylation zone 143 via line 145 and is reacted with the benzene to form ethylbenzene. Low molecular weight molecules, such as ethylene and ethane, are withdrawn from ethylation zone 143 via line 147. Ethylbenzene-containing product is withdrawn from ethylation zone 143 via line 149 and introduced into column 151. In column 151, the ethylbenzene-containing product is fractionated to form a $C_7-$ fraction and a $C_8+$ fraction comprised of ethylbenzene and polyethylbenzenes. The $C_7-$ fraction is withdrawn from column 151 via line 153 and is either removed via line 155 or recycled via line 141 to ethylation zone 143. The $C_8+$ fraction is withdrawn from column 151 via line 157 and introduced into column 159. In Column 159, the $C_8+$ fraction is fractionated into a high purity ethylbenzene product fraction and a $C_9+$ fraction comprised of polyethylbenzenes. The high purity ethylbenzene product fraction is withdrawn from column 159 via line 161 and recovered without need for further purification. The ethylbenzene product will usually have a purity that exceeds 99.50 percent by weight based on the total weight of the product.

The remaining $C_9+$ fraction can undergo further processing. As exemplified in FIG. 3, the $C_9+$ fraction is withdrawn from column 159 via line 163 and introduced into column 165. In column 165, polyethylbenzenes are separated from $C_{13}+$ hydrocarbons. The $C_{13}+$ hydrocarbon fraction is withdrawn from column 165 via line 167 and the polyethylbenzenes are withdrawn from column 165 via line 169 and transferred to transalkylation zone 171. In transalkylation zone 171, the polyethylbenzenes are transalkylated with benzene to form ethylbenzene. Benzene can be introduced into transalkylation zone 171 via line 173 or the benzene can be a fresh supply. The transalkylation product of transalkylation zone 171 is transferred to column 151 via lines 175 and 149 for processing.

Ethylation Catalyst

In a preferred embodiment, the catalyst used in ethylating benzene will be acid-active catalyst comprising a crystalline MCM-22 family material. These molecular sieves are described in detail in "Atlas of Zeolite Framework Types", eds. Ch. Baerlocher, W. H. Meier, and D. H. Olson, Elsevier, Fifth Revised Edition, 2001, which is hereby incorporated by reference. Examples of MCM-22 family molecular sieves include MCM-22, MCM-36, MCM-49, MCM-56, ITQ-1, SSZ-25, and PSH-3. Preferably, the molecular sieve is MCM-22, and, most preferably, the molecular sieve is aluminosilicate MCM-22.

The acid-active catalyst used in this disclosure will usually have an alpha value in the range of from about 1 to about 1000, preferably from about 10 to about 1000, more preferably from about 100 to about 1000.

In some aspects, the acid-active catalyst used in this disclosure may comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5 is described in detail in U.S. Pat. No. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. The entire contents of all the above patent specifications are incorporated herein by reference.

In some other aspects, the acid-active catalyst used in this disclosure may comprise a large pore molecular sieve having a Constraint Index of less than 2. Suitable large pore molecular sieves include zeolite beta, zeolite Y, Ultrastable Y (USY), Dealuminized Y (DealY), mordenite, ZSM-3, ZSM-4, ZSM- 18, a MCM-22 family material, and ZSM-20. Zeolite ZSM-14 is described in U.S. Pat. No. 3,923,636. Zeolite ZSM-20 is described in U.S. Pat. No. 3,972,983. Zeolite beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

In some embodiments, the acid-active catalyst may comprise a mixture of at least one medium pore molecular sieve having a Constraint Index of 2-12 and at least one large pore molecular sieve having a Constraint Index of less than 2.

The molecular sieve present in the catalyst will usually have an alpha value in the range of from about 100 to about 1000. The alpha value is a measure of molecular sieve acidic functionality and is described together with details of its measurement in U.S. Pat. No. 4,016,218 and in J. Catalysis, Vol. VI, pp. 278-287 (1966) and reference is made to these for such details. Higher alpha values correspond with a more active cracking catalyst.

The transalkylation catalyst may comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35, and ZSM-48. ZSM-5, a large pore molecular sieve having a Constraint Index of less than 2. Suitable large pore molecular sieves include zeolite beta, MCM-22 family material, zeolite Y, Ultrastable Y (USY), Dealuminized Y (Deal Y), mordenite, ZSM-3, ZSM-4, ZSM-18, and ZSM-20. or any combination thereof.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the constraint index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which Constraint Index may be determined is described fully in U.S. Pat. No. 4,016,218, which is incorporated herein by reference.

Usually the crystalline molecular sieve will be combined with binder material resistant to the temperature and other conditions employed in the process. Examples of suitable binder material include clays, alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The molecular sieve may also be composited with zeolitic material such as the zeolitic materials which are disclosed in U.S. Pat. No. 5,993,642, which is hereby incorporated by reference.

The relative proportions of molecular sieve and binder material will vary widely with the molecular sieve content ranging from between about 1 to about 99 percent by weight, more preferably in the range of about 10 to about 70 percent by weight of molecular sieve, and still more preferably from about 40 to about 70 percent.

Aromatization

Aromatization will usually be carried out by the dehydrocyclo-oligomerization of $C_2$-$C_5$ aliphatics, catalytic reforming of naphtha, or the cracking of hydrocarbons.

Dehydrocyclo-oligomerization involves converting $C_2$-$C_5$ aliphatic hydrocarbons to aromatic hydrocarbons. The process is carried out by contacting $C_2$-$C_5$ aliphatic hydrocarbons in an aromatization zone and in the presence of a catalyst suitable for dehydrocyclodimerization and under conditions effective to produce an aromatics product comprising benzene and/or toluene. The dehydrocyclodimerization process increases carbon chain length by oligomerization, promotes cyclization, and dehydrogenates cyclics to their respective aromatics.

The feedstream used in the dehydrocyclo-oligomerization process will contain at least one aliphatic hydrocarbon containing 2 to about 5 carbon atoms. The aliphatic hydrocarbons may be open chain, straight chain, or cyclic. Examples of such hydrocarbons include ethane, ethylene, propane, propylene, n-butane, n-butenes, isobutane, isobutene, butadiene, straight and branched pentane, pentene, and pentadiene. Dehydrocyclo-oligomerization conditions will vary depending on such factors as feedstock composition and desired conversion. A desired range of conditions for the dehydrocyclodimerization of the aliphatic hydrocarbons to aromatics include a temperature from about 350° to about 750° C., a pressure from about 101.3 kPa-a to about 10.13 MPa-a, and weight hour space velocity from about 0.2 to about 8. It is understood that, as the average carbon number of the feed increases, a temperature in the lower end of temperature range is required for optimum performance and conversely, as the average carbon number of the feed decreases, the higher the required reaction temperature.

The catalyst used in the dehydrocyclo-oligomerization reaction will preferably comprise an intermediate pore size molecular sieve. Intermediate pore size molecular sieves have a pore size from about 5 to about 7 Å and include, for example, AEL, AFI, MWW, MFI, MEL, MFS, MEI, MTW, EUO, MTT, HEU, FER, and TON structure type molecular sieves. These materials are described in "Atlas of Zeolite Structure Types", eds. W. H. Meier, D. H. Olson, and Ch. Baerlocher, Elsevier, Fourth Edition, 1996, which is hereby incorporated by reference. Examples of suitable intermediate pore size molecular sieves include ZSM-5, ZSM-11, ZSM-12, ZSM-22, ZSM-23, ZSM-34, ZSM-35, ZSM-38, ZSM-48, ZSM-50, ZSM-57, MCM-22, MCM-49, MCM-56, and SAPO-5. Preferred molecular sieves are SAPO-11, as well as titanosilicate, gallosilicate, aluminosilicate, and gallium-containing aluminosilicate molecular sieves having a MFI structure.

Usually the molecular sieve will be combined with binder material resistant to the temperature and other conditions employed in the process. Suitable binder material and relative proportions of molecular sieve and binder material are the same as those described above for the catalyst used for the propylation of benzene.

When the hydrocarbon composition feed used in the present disclosure is made from reformate produced by catalytic reforming, the reformats will usually be formed by contacting a $C_6+$ paraffinic feed, e.g., naphtha, with a reforming catalyst under reforming conditions to produce a reaction product comprising benzene and other hydrocarbons. The reformate is formed under typical reforming conditions designed to promote dehydrogenation of naphthenes, isomerization of paraffinic hydrocarbons and dehydrocyclization of non-aromatic hydrocarbons.

Substantially any hydrocarbon feed containing $C_6+$ paraffins, e.g., naphtha, can be utilized as feedstock for naphtha reforming. The naphtha will generally comprise $C_6$-$C_9$ aliphatic hydrocarbons. The aliphatic hydrocarbons may be straight or branched chain acyclic hydrocarbons, and particularly paraffins such as heptane.

Catalysts suitable for use in catalytic reforming include acidic reforming catalysts (bifunctional catalysts) and non-acidic reforming catalysts (monofunctional catalysts).

Acidic reforming catalysts usually comprise a metallic oxide support having disposed therein a Group 8, 9, or 10 metal. Suitable metallic oxide supports include alumina and silica. Preferably, the acidic reforming catalyst comprises a metallic oxide support having disposed therein in intimate admixture a Group 8, 9, or 10 metal (preferably platinum) and a metal promoter, such as rhenium, tin, germanium, cobalt, nickel, iridium, rhodium, ruthenium and combinations thereof. More preferably, the acidic reforming catalyst comprises an alumina support, platinum, and rhenium or platinum and tin on an alumina support.

Non-acidic or monofunctional reforming catalysts will comprise a non-acidic molecular sieve, e.g., zeolite, and one or more hydrogenation/dehydrogenation components. Examples of suitable molecular sieves include MFI structure type, e.g., silicalite, and molecular sieves having a large pore size, e.g., pore size from about 7 to 9 Angstroms. Examples of large pore molecular sieves include LTL, FAU, and *BEA structure types. Examples of specific molecular sieves include zeolite L, zeolite X, zeolite Beta, zeolite Y, and ETS-10.

The reforming catalysts will contain one or more hydrogenation/dehydrogenation metals, e.g., Group 7 metals, such as rhenium, and Group 8, 9, or 10 metals, such as nickel, ruthenium, rhodium, palladium, iridium or platinum. The preferred Group 8, 9, or 10 metal is platinum. Also, the nonacidic catalyst can contain a metal promoter such as tin.

The amount of hydrogenation/dehydrogenation metal present on the non-acidic catalyst will usually be from about 0.1% to about 5.0% of hydrogenation/dehydrogenation metal based on the weight of the catalyst. The metal can be incorporated into the zeolite during synthesis of the zeolite, by impregnation, or by ion exchange of an aqueous solution containing the appropriate salt. By way of example, in an ion exchange process, platinum can be introduced by using cationic platinum complexes such as tetraammine-platinum (II) nitrate.

The non-acidic catalyst will usually include a binder. The binder can be a natural or a synthetically produced inorganic oxide or combination of inorganic oxides. Typical inorganic oxide supports which can be used include clays, alumina, and silica, in which acidic sites are preferably exchanged by cations that do not impart strong acidity.

The reforming process can be continuous, cyclic or semi-regenerative. The process can be in a fixed bed, moving bed, tubular, radial flow or fluid bed.

Conditions for reforming conditions include temperatures of at least about 400° C. to about 600° C. and pressures from about 344.7 kPa-a to about 3.447 MPa-a, a mole ratio of hydrogen to hydrocarbons from 1:1 to 10:1 and a liquid hour space velocity of between 0.3 and 10.

When the hydrocarbon composition feed used in the present disclosure is made from reformate produced by steam cracking, the reformate will usually be formed by contacting a $C_6+$ paraffinic feed, e.g., naphtha, and steam under steam cracking conditions to produce a reaction product comprising benzene and other hydrocarbons. The reformate is formed under typical steam cracking conditions designed to promote thermal conversion of paraffins to light olefins and aromatics.

Substantially any hydrocarbon feed containing $C_2+$ paraffins, e.g., ethane, propane, butanes, naphtha, distillate, atmospheric gas oil, vacuum gas oil, and/or any combination can be utilized as feedstock for steam cracking. The naphtha will generally comprise $C_6$-$C_9$ non-aromatic hydrocarbons. The non-aromatic hydrocarbons may be straight or branched chain cyclic and acyclic hydrocarbons, and particularly cyclic hydrocarbons such as methylcyclopentadiene.

The hydrocarbon composition will contain from about 1 to about 75 percent by weight of at least one benzene coboiler, i.e., $C_6+$ non-aromatic hydrocarbons having a boiling point within 10° C. at a pressure of about 101.3 kPa-a of the boiling point of benzene. Some hydrocarbon compositions will contain different amounts of benzene coboilers, e.g., about 5 to about 60 percent by weight of the at least one benzene coboiler or from about 10 to about 50 percent by weight of the at least one benzene coboiler. Also in some hydrocarbon compositions, the $C_6+$ non-aromatic hydrocarbons present in the hydrocarbon composition will have a boiling point within 5° C. at a pressure of about 101.3 kPa-a of the boiling point of benzene.

Examples of benzene coboilers that can be present in the hydrocarbon composition feed to the propylation unit include cyclopentane, cyclohexane, methylcyclopentane, 2-methylhexane, 3-methylhexane, 2,3-dimethylpentane, 2,4-dimethylpentane, and dimethylcyclopentane.

Feed Pretreatment

The hydrocarbon composition feed used in the process of the present disclosure may contain impurities such as, for example, olefins, dienes, sulfur-containing compounds, nitrogen-containing compounds, and combinations thereof. Preferably, at least a portion of one or more of these impurities is removed from the hydrocarbon composition feed before propylation of benzene to extend the cycle length of the catalyst and to reduce the formation of ethylbenzene co-boilers in the product of the propylation reactor.

Techniques for removing these impurities are known to persons skilled in the art. Nitrogen-containing and sulfur-containing impurities can be removed by hydroprocessing. Hydroprocessing techniques are well known in the art and are often required to enable steam cracker naphtha to be blended into gasoline that meets U.S. low sulfur gasoline specifications. Hydroprocessing is carried out by treating a hydrocarbon feed with hydrogen in the presence of a supported catalyst at hydrotreating conditions. The catalyst is usually comprised of a Group 6 metal with one or more Group 8, 9, or 10 metals as promoters on a refractory support. In a preferred embodiment, steam cracker naphtha is hydrotreated to reduce sulfur levels to less than 5 wppm, nitrogen levels to less than 1 wppm, and olefin and diene levels to less than 2500 wppm. Hydroprocessing produces a naphtha from steam cracking with very similar levels of impurities to the naphtha produced from naphtha reforming. Techniques for subsequently removing the olefins and dienes (from either reformate or hydroprocessed steam cracker naphtha) are disclosed in U.S. Pat. Nos. 6,781,023 and 6,500,996, which are incorporated by reference. A preferred technique for removing olefins and dienes involves contacting the hydrocarbon composition feed containing olefins/dienes with a crystalline molecular sieve catalyst comprising MCM-22.

Nitrogen-containing and sulfur-containing impurities can also be removed by contacting the nitrogen-containing and sulfur-containing hydrocarbon composition feed with an absorbent under absorption conditions effective to remove at least a portion of the nitrogen-containing/sulfur-containing impurities. Example of suitable absorbents include clay materials and alumina compounds. Preferred absorption conditions include a temperature of from ambient to 500° C., more preferably from ambient to 200° C., or most preferably from ambient to 100° C.; a pressure sufficient to maintain liquid phase conditions; a weight hourly space velocity from 0.5 hr$^{-1}$ to about 100 hr$^{-1}$, more preferably from about 0.5 hr$^{-1}$ to about 10 hr$^{-1}$, most preferably from 1.0 hr$^{-1}$ to 4.0 hr$^{-1}$ depending upon the hydrocarbon composition feed being treated.

Process

Suitable alkylating agent(s) that may be used in this disclosure comprise alkene compound(s), alcohol compound(s), and/or alkylbenzene(s), and mixtures thereof. Other suitable alkylating agents that may be useful in the process of this disclosure generally include any aliphatic or aromatic organic compound having one or more available alkylating aliphatic groups capable of reaction with the alkylatable aromatic compound. Examples of suitable alkylating agents comprise $C_2$ olefin, viz., ethylene; $C_2$ alkanol; $C_2$ ethers, e.g., $C_2$-$C_5$ ethers including methylethylether and diethylether; aldehydes such as acetaldehyde; alkyl halides such as ethyl chloride; and polyalkylated aromatic compound(s), e.g., bi-alkylated benzenes (e.g., bi-ethylbenzene(s)) and tri-alkylated benzene(s) (e.g., tri-ethylbenzenes), and so forth. Thus the alkylating agent may preferably be selected from the group consisting of $C_2$, $C_1$-$C_5$ alkanols, bi-ethylbenzene(s), and tri-ethylbenzene(s). The alkylating agent includes a concentrated alkene feedstock (e.g., polymer grade olefins) and a dilute alkene feedstock (e.g., catalytic cracking off-gas).

The alkylation reaction may also take place with the alkylatable aromatic compound and the alkylating agent in the reaction zone under conditions of at least partially in liquid phase. The alkylation or transalkylation conditions include a temperature of 100 to 285° C., preferably from about 162.8° C. to about 232.2° C., and a pressure of 689 to 6.89 MPa-a, preferably, a pressure of 1500 to 3000 kPa-a, a WHSV based on alkylating agent (e.g., alkene) for overall reactor of 0.1 to 10 h$^{-1}$, preferably, 0.2 to 2 h$^{-1}$, more preferably, 0.5 to 1 h$^{-1}$, or a WHSV based on both alkylating agent and alkylatable aromatics for overall reactor of 10 to 100 h$^{-1}$, preferably, 20 to 50 h$^{-1}$, a mole ratio of ethylene to benzene of from about 0.01:1 to about 0.5:1, and a WHSV based on total ethylene over total catalyst for overall reactor of from about 0.5 and about 2 hr$^1$. More preferably, the mole ratio of ethylene to benzene is in the range of from about 0.02:1 to about 0.4:1. Most preferably, mole ratio of ethylene to benzene is about 0.03. The alkylatable aromatic compound is alkylated with the alkylating agent (e.g., alkene) in the presence of an alkylation or transalkylation catalyst in a reaction zone or a plurality of reaction zones. The reaction zone(s) are preferably located in a single reactor vessel, but may include another reaction zone having an alkylation or transalkylation catalyst bed, located in separate vessel which may be a by-passable and which may operate as a reactive guard bed. The catalyst composition used in the reactive guard bed may be different from the catalyst composition used in the reaction zone. The catalyst composition used in the reactive guard bed may have multiple catalyst compositions. At least one reaction zone, and normally each reaction zone, is maintained under conditions effective to cause alkylation of the alkylatable aromatic compound with the alkylating agent in the presence of an alkylation or transalkylation catalyst.

Particular conditions for carrying out the alkylation of benzene with ethylene at least partially in liquid phase may have a temperature of from about 120 to 285° C., preferably, a temperature of from about 150 to 260° C., a pressure of 689 to 4601 kPa-a, preferably, a pressure of 1500 to 4137 kPa-a, a WHSV based on total ethylene and total catalyst for overall reactor of 0.1 to 10 h$^{-1}$, preferably, 0.2 to 2 h$^{-1}$, more preferably, 0.5 to 1 h$^{-1}$, or a WHSV based on both total ethylene and benzene, and total catalyst for overall reactor of 10 to 100 h$^{-1}$, preferably, 20 to 50 h$^{-1}$, and a molar ratio of benzene to ethylene from about 1 to about 100, preferably from about 20 to about 80.

In some embodiments, the benzene is alkylated with ethylene to produce ethylbenzene in the liquid phase. Suitable liquid phase conditions include a temperature between about 150° C. and 316° C., preferably between about 205° C. and 260° C., a pressure up to about 20875 kPa-a, preferably between 2860 and 5600 kPa-a, a space velocity between about 0.1 and 20 h$^{-1}$ WHSV, preferably between 1 and 6 h$^{-1}$ WHSV, based on the ethylene feed, and a ratio of the benzene to the ethylene in the alkylation reactor from about 0.5:1 to about 100:1 molar, preferably 0.5:1 to 50:1 molar, more preferably from about 1:1 to about 30:1 molar, most preferably from about 1:1 to about 10:1 molar.

The alkylating agent, e.g., ethylene, to benzene ratios specified for use in the process of the present disclosure refers to the mole ratio of alkylating agent, e.g., ethylene, to benzene at the reactor inlet. For example, in case of a reactor having more than one catalyst bed, e.g., four beds, with ethylene feed being injected into each bed, the mole ratio of ethylene to benzene injected into each bed will be within the specified range, i.e., ethylene to benzene mole ratio will be within a range defined by a lower number and a high number. For any specific range defined by a lower number and a high number, the lower number will be equal or lower than the higher end number, A range useful for this disclosure may be defined by any combination of two numbers selected from the group consisting of 0.001:1, 0.01:1, 0.015:1, 0.2:1, 0.025:1, 0.3:1; 0.31:1, 0.35:1, 0.4:1, 0.45:1, 0.5:1, 0.55:1, 0.6:1, 0.65:1, 0.7:1, 0.75:1, 0.8:1, 0.85:1, 0.9:1, 0.95:1, and 1:1. Examples of typical range are 0.001:1 to 0.75:1, 0.01:1 to 0.6:1; 0.02:1 to 0.5:1; 0.02:1 to 0.4:1; 0.02:1 to 0.3:1; and 0.02:1 to 0.1:1.

The process of the present disclosure produces an ethylbenzene product that contains at least 99.50 weight percent of ethylbenzene based on the weight of the product. Preferably, the process of the present disclosure produces an ethylbenzene product that contains at least 99.65 weight percent of ethylbenzene based on the weight of the product, more preferably the ethylbenzene product has a purity of at least 99.85 weight percent, and most preferably the ethylbenzene product has a purity of at least 99.95 weight percent. To further enhance the purity of the ethylbenzene product, the product can be blended with higher purity ethylbenzene product. For example, an ethylbenzene product having 99.85 weight percent purity can be increased to 99.985 weight percent purity by blending appropriate amounts of higher purity ethylbenzene product (100 percent ethylbenzene product) with the 99.85 purity product.

Distillation temperatures for separation, e.g., separation of polyethylbenzene from ethylbenzene, are known to persons skilled in the art and will depend upon the composition of the polyethylbenzene/ethylbenzene product.

The process of the present disclosure includes recovery of polyethylbenzenes as a separate fraction followed by transalkylating the polyethylbenzenes with benzene to form ethylbenzene.

The effluent from the reaction zone comprises the desired ethylbenzene, unreacted benzene, any unreacted ethylene (ethylene conversion is expected to be at least 90 mol. %, preferably, about 98-99.9999 mol. %) and the alkane component and the other impurities. In one embodiment, at least a portion of the effluent is fed to another reaction zone where additional ethylene is added for reaction with the unreacted benzene with an alkylation catalyst. Furthermore, at least a portion the effluent from any of the reaction zone(s) may be fed directly or indirectly to a transalkylation unit.

In addition to, and upstream of, the reaction zones, a by-passable reactive or unreactive guard bed may normally be located in a reactor separate from the alkylation reactor. Such guard bed may also be loaded with an alkylation or transalkylation catalyst, which may be the same or different from the catalyst used in the reaction zone(s). Such guard bed is maintained from under ambient conditions, or at suitable alkylation or transalkylation conditions. At least a portion of benzene, and optionally at least a portion of the ethylene, are passed through the unreactive or reactive guard bed prior to entry into the reaction zone. These guard beds not only serve to affect the desired alkylation reaction, but is also used to remove any reactive impurities in the hydrocarbon composition feeds, such as nitrogen compounds, which could otherwise poison the remainder of the alkylation or transalkylation catalyst. The catalyst in the reactive or unreactive guard bed may therefore be subject to more frequent regeneration and/or replacement than the remainder of the alkylation or transalkylation catalyst, and hence the guard bed is typically provided with a by-pass circuit so that the alkylation feed(s) may be fed directly to the series connected reaction zones in the reactor while the guard bed is out of service. The reactive or unreactive guard bed may be operated in co-current upflow or downflow operation.

The reaction zone(s) used in the process of the present invention is typically operated so as to achieve essentially complete conversion of the ethylene. However, for some applications, it may be desirable to operate at below 100% ethylene conversion. The employment of a separate finishing reactor downstream of the reaction zone(s) may be desirable under certain conditions. The finishing reactor would also contain alkylation or transalkylation catalyst, which could be the same or different from the catalyst used in other reaction zones in the alkylation or transalkylation reactor(s) and may be maintained under at least partially liquid phase or alternately vapor phase alkylation or transalkylation conditions. The polyalkylated aromatic compounds in the effluents may be separated for transalkylation with alkylatable aromatic compound(s). The alkylated aromatic compound is made by transalkylation between polyalkylated aromatic compounds and the alkylatable aromatic compound.

The alkylation or transalkylation reactor(s) used in the process of the present invention may be highly selective to the desired monoalkylated product, such as ethylbenzene, but typically produces at least some polyalkylated species. In one embodiment, at least a portion of the effluent from the final alkylation reaction zone is subjected to a separation step to recover polyalkylated aromatic compound(s). In another embodiment, at least a portion of the polyalkylated aromatic compound is supplied to a transalkylation reactor which may be separate from the alkylation reactor. The transalkylation reactor produces an effluent which contains additional monoalkylated product by reacting the polyalkylated species with an alkylatable aromatic compound. At least a portion of these effluents may be separated to recover the alkylated aromatic compound (monoalkylated aromatic compound and/or polyalkylated aromatic compound).

Where the alkylation system includes a reactive guard bed, it is maintained under at least partial in liquid phase conditions. The guard bed will preferably operate at a temperature of from about 120 to 285° C., preferably, a temperature of from about 150 to 260° C., a pressure of 689 to 4601 kPa-a), preferably, a pressure of 1500 to 4137 kPa-a, a WHSV based on total ethylene and the total amount of catalyst for the overall reactor of 0.1 to 10 h$^{-1}$, preferably, 0.2 to 2 h$^{-1}$, more preferably, 0.5 to 1 h$^{-1}$, or a WHSV based on both total ethylene and total benzene, and the total amount of catalyst for the overall reactor of 10 to 100 h$^{-1}$, preferably, 20 to 50 h$^{-1}$, and a molar ratio of benzene to ethylene from about 1 to about 100, preferably from about 20 to about 80.

The transalkylation reaction may take place under at least partially in liquid phase conditions. Particular conditions for carrying out the at least partially in liquid phase transalkylation of polyalkylated aromatic compound(s), e.g., polyisopropylbenzene(s), with benzene may include a temperature of from about 100° to about 300° C., a pressure of 696 to 4137 kPa-a, a WHSV based on the weight of the polyalkylated aromatic compound(s) feed to the alkylation reaction zone of from about 0.5 to about 100 hr$^{-1}$ and a molar ratio of benzene to polyalkylated aromatic compound(s) of from 1:1 to 30:1, preferably, 1:1 to 10:1, more preferably, 1:1 to 5:1.

In another embodiment, the transalkylation reaction may take place under vapor phase conditions. Particular conditions for carrying out the vapor phase transalkylation of polyalkylated aromatic compound(s), polyisopropylbenzene(s), with benzene may include a temperature of from about 350 to about 450° C., a pressure of 696 to 1601 kPa-a, a WHSV based on the weight of the polyalkylated aromatic compound(s) feed to the reaction zone of from about 0.5 to about 20 hr$^{-1}$, preferably, from about 1 to about 10 hr$^{-1}$, and a molar ratio of benzene to polyalkylated aromatic compound(s) of from 1:1 to 5:1, preferably, 2:1 to 3:1.

In some embodiments, this disclosure relates to:

1. A process for producing an ethylbenzene product having a purity of at least 99.50 percent based on the weight of cumene present in the product using a hydrocarbon composition feed that has not undergone extraction, is substantially free of $C_4$– hydrocarbons and $C_7$+ aromatic hydrocarbons, and contains benzene and from about 1 to about 75 percent by weight of at least one $C_6$+ non-aromatic hydrocarbon having a boiling point within 10° C. at a pressure of about 101.3 kPa-a of the boiling point of benzene, said process comprising:
    (a) alkylating the benzene with ethylene in an alkylation reaction zone, said reaction zone is maintained under at least partial liquid phase conditions, with an acid-active catalyst at conditions that include a temperature in the range of from about 125° C. to about 285° C., a pressure sufficient to maintain the mixture of benzene and ethylene in at least partial liquid phase, a mole ratio of ethylene to benzene in the range of from about 0.001:1 to about 0.75:1, and a WHSV based on total ethylene over total catalyst for overall reactor in the range of from about 0.1 to about 10 hr$^1$; and
    (b) distilling the product of step (a) to produce an ethylbenzene product having a purity of at least 99.50 percent based on the weight of ethylbenzene present in said ethylbenzene product.
2. The process recited in Paragraph 1, wherein said hydrocarbon composition feed is produced from a reformate.
3. The process recited in Paragraph 2, wherein said reformate comprises: (i) $C_5$– hydrocarbons; (ii) benzene; (iii) $C_7$+ aromatic hydrocarbons; and (iv) from about 1 to about 75 percent by weight of at least one $C_6$+ non-aromatic hydrocarbon having a boiling point within 10° C. at a pressure of about 101.3 kPa-a of the boiling point of benzene and said hydrocarbon composition feed is prepared from said reformate by removing by distillation the $C_4$- hydrocarbons and said $C_7$+ aromatic hydrocarbons from said reformate.
4. The process as recited in any preceding paragraph, further comprising recovering polyethylbenzenes from the product of step (a).
5. The process as recited in Paragraph 4, further comprising transferring said polyethylbenzenes to a transalkylation zone and reacting the polyethylbenzenes with benzene under transalkylation conditions to form ethylbenzene.
6. The process as recited in Paragraph 5, wherein said ethylbenzene produced by the reaction of the polyethylbenzenes with benzene is transferred to said alkylation reaction zone.
7. The process as recited in Paragraph 5, wherein said benzene is reacted with polyethylbenzenes in said transalylation zone is supplied from said hydrocarbon composition feed.
8. The process recited in any preceding paragraph, wherein the alkylation conditions include a temperature of from about 182° C. to about 216° C., a pressure of from about 1479.6 kPa-a to about 2858.6 kPa-a, a mole ratio of ethylene to benzene of from about 0.01:1 to about 0.5:1, and a WHSV based on total ethylene over total catalyst for overall reactor of from about 0.5 and about 2 $hr^1$.
9. The process recited in Paragraph 8, wherein said mole ratio of ethylene to benzene is from about 0.02:1 to about 0.4:1.
10. The process recited in Paragraph 9, wherein said mole ratio of ethylene to benzene is about 0.03.
11. The process as recited in any preceding paragraph, wherein said acid active catalyst comprises at least one of a MCM-22 family material and a zeolite beta molecular sieve.
12. The process as recited in any preceding paragraph, wherein said catalyst further comprises a binder.
13. The process as recited in Paragraph 12, wherein said MCM-22 family material is selected from the group consisting of MCM-22, MCM-36, MCM-49, and MCM-56.
14. The process as recited in any preceding paragraph, wherein said at least one $C_6$+ non-aromatic hydrocarbon is selected from the group consisting of cyclohexane, methylcyclopentane, 2-methylhexane, 3-methylhexane, 2,3-dimethylpentane, 2,4-dimethylpentane, dimethylcyclopentane, and mixtures thereof.
15. The process recited in any preceding paragraph, wherein said purity of said ethylbenzene product is at least 99.85 percent based on the weight of ethylbenzene present in the product.
16. The process recited in Paragraph 15, wherein said purity of said ethylbenzene product is at least 99.985 percent based on the weight of ethylbenzene present in the product.
17. The process recited in any one of Paragraphs 2-16, wherein said reformate is formed by the catalytic reforming of naphtha.
18. The process recited in any one of Paragraphs 2-16, wherein said reformate is formed by the cracking of hydrocarbons.
19. The process as recited in Paragraph 18, wherein said cracking is accomplished by steam cracking.
20. The process as recited in any preceding paragraph, wherein said at least one $C_6$+ non-aromatic hydrocarbon is present in said hydrocarbon composition feed in an amount 5 to about 60 percent by weight of at least one $C_6$+ non-aromatic hydrocarbon having a boiling point within 10° C. at a pressure of about 101.3 kPa-a of the boiling point of benzene.
21. The process as recited in Paragraph 20, wherein said at least one $C_6$+ non-aromatic hydrocarbon is present in said hydrocarbon composition feed in an amount 10 to about 50 percent by weight of at least one $C_6$+ non-aromatic hydrocarbon having a boiling point within 10° C. at a pressure of about 101.3 kPa-a of the boiling point of benzene.
22. The process as recited in any preceding paragraph, wherein said hydrocarbon composition feed contains impurities selected from the group consisting of olefins, dienes, sulfur-containing compounds, nitrogen-containing compounds, and mixtures thereof and at least a portion of at least one of said impurities are removed from the feed prior to contact with said catalyst.
23. A process for producing an ethylbenzene product having a purity of at least 99.50 percent based on the weight of ethylbenzene present in the product using a hydrocarbon composition that has not undergone extraction, said process comprising:
(a) providing a reformate that comprises: (i) $C_5$- hydrocarbons; (ii) benzene; (iii) $C_7$+ aromatic hydrocarbons; and (iv) from about 1 to about 75 percent by weight based on the weight of the reformate of at least one $C_6$+ non-aromatic hydrocarbon having a boiling point within 10° C. at a pressure of about 101.3 kPa-a of the boiling point of benzene;
(b) removing $C_4$- hydrocarbons and the $C_7$+ aromatic hydrocarbons from the reformate by distillation to form a hydrocarbon composition;
(c) alkylating the benzene present in the hydrocarbon composition without extraction of the hydrocarbon composition with ethylene in the liquid phase with a catalyst comprising at least one of a MCM-22 family molecular sieve and a zeolite beta molecular sieve at conditions that include a temperature in the range of from about 163° C. to about 232° C., a pressure sufficient to maintain the benzene in the liquid phase, usually at least 0.79 MPa-a, e.g., from about 0.79 to about 6.995 MPa-a, a mole ratio of ethylene to benzene in the range of from about 0.001:1 to about 0.75:1, and a WHSV based on total ethylene over total catalyst for overall reactor in the range of from about 0.1 to about 10 $h^1$; and
(d) distilling the product of step (c) to produce an ethylbenzene product having a purity of at least 99.50 percent based on the weight of ethylbenzene present in the product.
24. The process recited in Paragraph 23, wherein the alkylation conditions include a temperature of from about 182° C. to about 216° C., a pressure of from about 1479.6 kPa-a to about 2858.6 kPa-a, a mole ratio of ethylene to benzene of from about 0.01:1 to about 0.65, and a WHSV based on total ethylene over total catalyst for overall reactor of from about 0.5 and about 2 $hr^1$.
25. The process recited in any one of Paragraphs 23-24, wherein said mole ratio of ethylene to benzene is from about 0.02:1 to about 0.4:1.
26. The process recited in Paragraph 25, wherein said mole ratio of ethylene to benzene is about 0.03.
27. The process as recited in any one of Paragraphs 23-26, wherein said MCM-22 family molecular sieve is selected from the group consisting of MCM-22, MCM-36, MCM-49, and MCM-56.
28. The process as recited in any one of Paragraphs 23-27, wherein said molecular sieve is MCM-22.
29. The process recited in any one of Paragraphs 23-28, wherein said reformate is formed by the catalytic reforming of naphtha.
30. The process recited in any one of Paragraphs 23-28, wherein said reformate is formed by the cracking of hydrocarbons.

31. The process recited in Paragraph 30, wherein said cracking is accomplished by steam cracking.
32. The process recited in any one of Paragraphs 23-28, wherein said purity of said ethylbenzene product is at least 99.85 percent based on the weight of ethylbenzene present in the product.
33. The process recited in any one of Paragraphs 23-28, wherein said purity of said ethylbenzene product is at least 99.985 percent based on the weight of ethylbenzene present in the product.
34. The process as recited in any one of Paragraphs 23-33, wherein said hydrocarbon composition feed contains impurities selected from the group consisting of olefins, dienes, sulfur-containing compounds, nitrogen-containing compounds, and mixtures thereof and at least a portion of at least one of said impurities are removed from the feed prior to contact with said catalyst.
35. The process as recited in any one of Paragraphs 23-34, further comprising recovering polyethylbenzenes from the product of step (c).
36. The process as recited in Paragraph 35, further comprising transferring said polyethylbenzenes to a transalkylation zone and reacting the polyethylbenzenes with benzene under transalkylation conditions to form ethylbenzene.
37. The process as recited in any one of Paragraphs 23-36, wherein said at least one $C_6+$ non-aromatic hydrocarbon is present in said hydrocarbon composition feed in an amount 5 to about 60 percent by weight of at least one $C_6+$ non-aromatic hydrocarbon having a boiling point within 10° C. at a pressure of about 101.3 kPa-a of the boiling point of benzene.
38. The process as recited in Paragraph 37, wherein said at least one $C_6+$ non-aromatic hydrocarbon is present in said hydrocarbon composition feed in an amount 10 to about 50 percent by weight of at least one $C_6+$ non-aromatic hydrocarbon having a boiling point within 10° C. at a pressure of about 101.3 kPa-a of the boiling point of benzene.

The following example illustrates certain embodiments of the present disclosure but is not intended to be construed as to be restrictive of the spirit and scope thereof.

EXAMPLE

Tests were carried out using a feed that comprised 49.5 weight percent benzene and 49.5 percent by weight of 2,3-dimethylpentane (remainder of the feed contained other reformate produced hydrocarbons) by passing the feed over a MCM-22 catalyst. The conditions of the first test (Test A) included a temperature from 176.7° C. to 204.4° C., a pressure of 1.72 MPa-a, ethylene to benzene mole ratio of 0.5:1, and a WHSV based on total ethylene over total catalyst for overall reactor between 2 to 10 $hr^{-1}$. The conditions in the second test (Test B) included a temperature from 176.7° C. to 204.4° C., a pressure of 1.72 MPa-a, ethylene to benzene mole ratio of 1:1, and a WHSV based on total ethylene over total catalyst for overall reactor between 2 to 10 $hr^{-1}$. Results of the tests are in FIG. 4 through FIG. 6.

Figure 4:
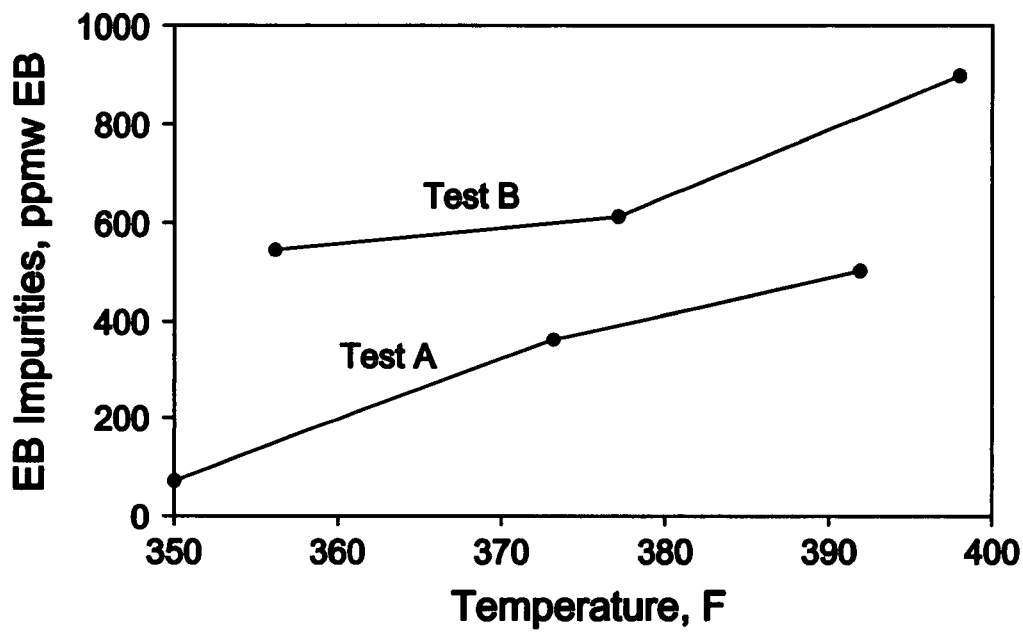
FIG. 4 is a graph plotting impurities present in the products of Test A and Test B of the Example.
Figure 5:
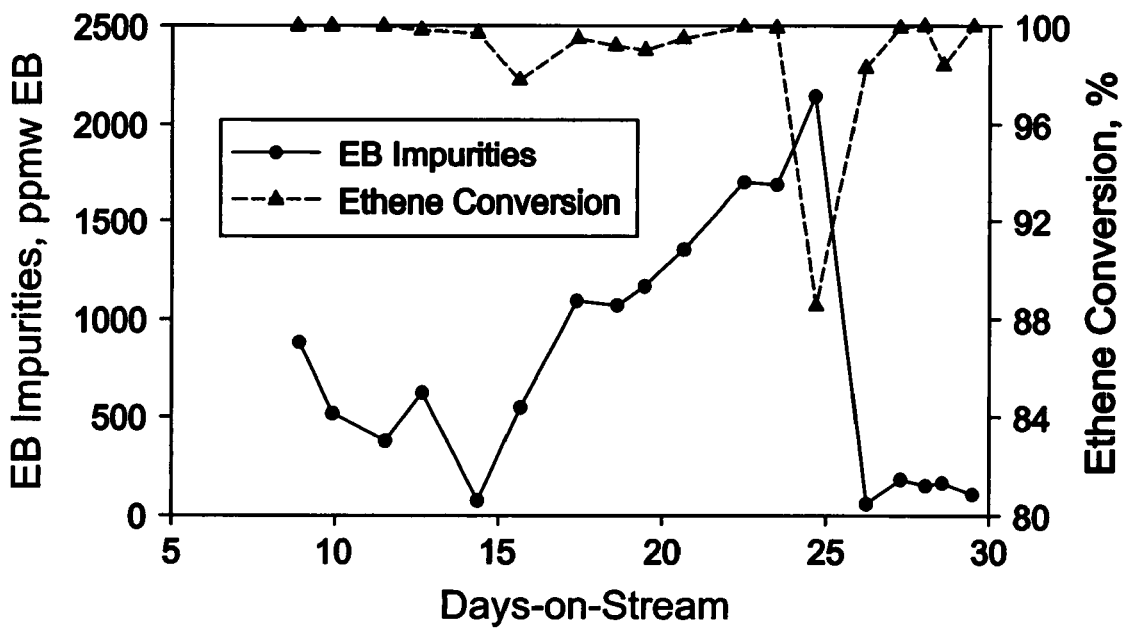
FIG. 5 is a graph illustrating aging of the catalyst used in Test A of the Example.
Figure 6:
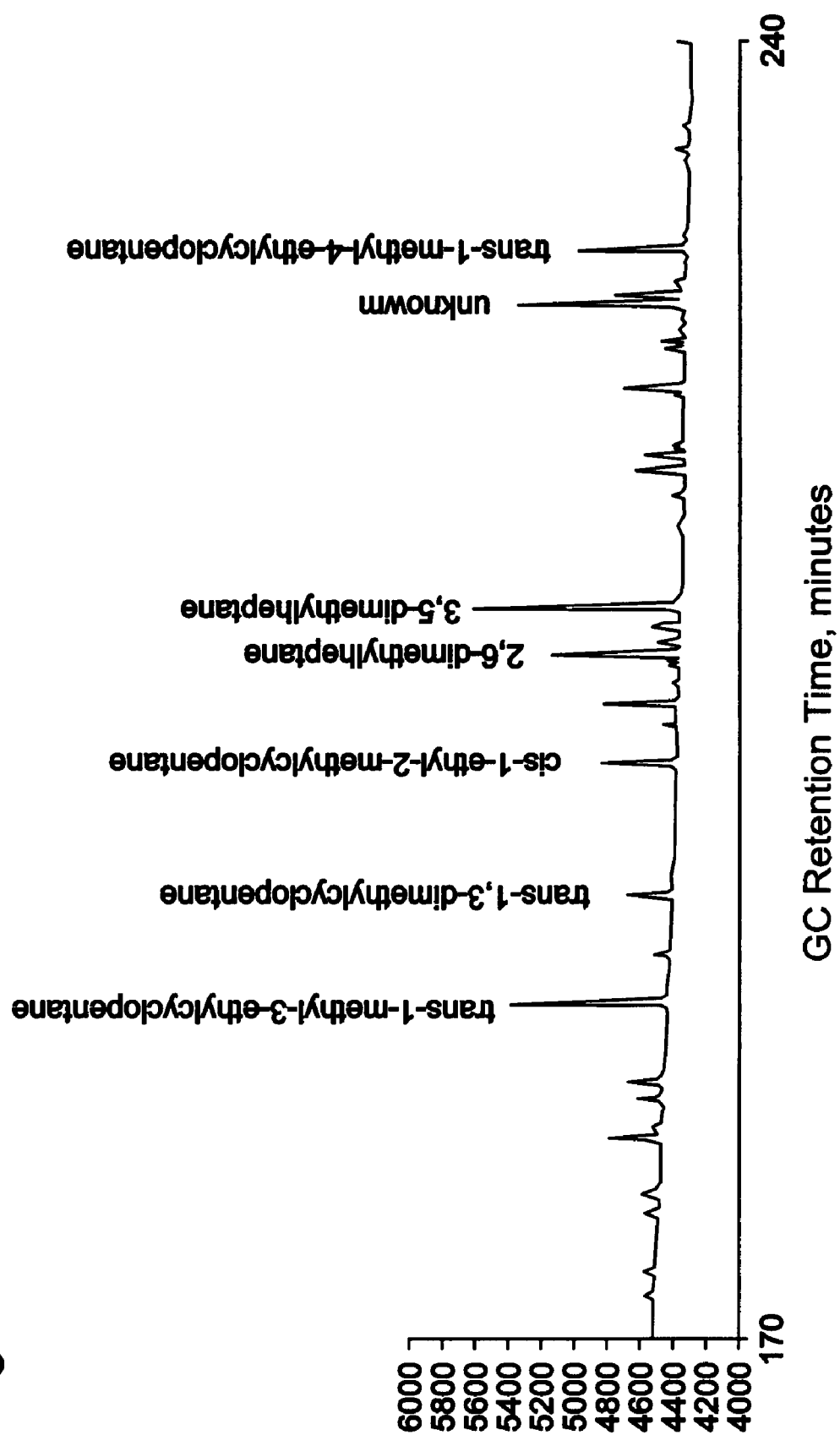
FIG. 6 is a gas chromatogram of impurities ethylbenzene coboilers formed by isoparaffin/olefin alkylation reactions.

FIG. 4 is a plot of impurities produced in the production of ethylbenzene vis à vis temperature and ethylene to benzene ratio and shows that the practice of the present disclosure resulted in the production of ethylbenzene product with low impurities. FIG. 5, which is a plot of the aging for the catalyst used in Test A, shows that process monitoring is important to maintain production of high purity ethylbenzene product. Impurities began increasing after about 14-15 days on stream. After 25 days on stream, catalyst regeneration was conducted by contacting the catalyst with a hydrocarbon wash. FIG. 6 is a gas chromatogram of the impurities present in the ethylbenzene product after the catalyst was on stream for 25 days.

The invention claimed is:

1. A process for producing an ethylbenzene product having a purity of at least 99.50 percent based on the weight of ethylbenzene present in the product using a hydrocarbon composition that has not undergone extraction, said process comprising:
   (a) providing a reformate that comprises: (i) $C_5$-hydrocarbons; (ii) benzene; (iii) $C_7+$ aromatic hydrocarbons; and (iv) from about 1 to about 75 percent by weight based on the weight of the reformate of at least one $C_6+$ non-aromatic hydrocarbon having a boiling point within 10° C. at a pressure of about 101.3 kPa-a of the boiling point of benzene;
   (b) removing $C_4-$ hydrocarbons and the $C_7+$ aromatic hydrocarbons from the reformate by distillation to form a hydrocarbon composition, wherein said hydrocarbon composition contains C5 hydrocarbons, benzene from about 1 to about 75 percent by weight based on the weight of the reformate of at least one $C_6+$ non-aromatic hydrocarbon having a boiling point within 10° C. at a pressure of about 101.3 kPa-a of the boiling point of benzene and substantially free of $C_4-$ hydrocarbons and $C_7+$ aromatic hydrocarbons;
   (c) alkylating the benzene present in the hydrocarbon composition without extraction of the hydrocarbon composition with ethylene in the liquid phase with a catalyst comprising a MCM-22 molecular sieve at conditions that include a temperature in the range of from about 176° C. to about 204° C., a pressure from about 0.79 to about 6.995 MPa-a sufficient to maintain the benzene in the liquid phase, a mole ratio of ethylene to benzene in the range of from about 0.75:1 to about 0.5:1, and a WHSV based on total ethylene over total catalyst for overall reactor in the range of from about 0.1 to about 10 $hr^{-1}$ to produce a product; and
   (d) distilling the product of step (c) to produce an ethylbenzene product having a purity of at least 99.50 percent based on the weight of ethylbenzene present in the product.

2. The process recited in claim 1, wherein said reformate is formed by the catalytic reforming of naphtha.

3. The process recited in claim 1, wherein said purity of said ethylbenzene product is at least 99.85 percent based on the weight of ethylbenzene present in the product.

4. The process as recited in claim 1, wherein said hydrocarbon composition feed contains impurities selected from the group consisting of olefins, dienes, sulfur-containing compounds, nitrogen-containing compounds, and mixtures thereof and at least a portion of at least one of said impurities are removed from the feed prior to contact with said catalyst.

5. The process as recited in claim 1, further comprising recovering polyethylbenzenes from the product of step (c).

6. The process as recited in claim 5, further comprising transferring said polyethylbenzenes to a transalkylation zone and reacting said polyethylbenzenes with benzene under transalkylation conditions to form ethylbenzene.

7. The process as recited in claim 6, wherein said ethylbenzene produced by said reaction of said polyethylbenzenes with benzene is transferred to said alkylation reaction zone.

8. The process as recited in claim 6, wherein said benzene reacted with said polyethylbenzenes in said transalkylation zone is supplied from said hydrocarbon composition feed.

9. The process as recited in claim 1, wherein said at least one $C_6+$ non-aromatic hydrocarbon is present in said hydrocarbon composition feed in an amount 5 to about 60 percent by weight of at least one $C_6+$ non-aromatic hydrocarbon having a boiling point within 10° C. at a pressure of about 101.3 kPa-a of the boiling point of benzene.

10. The process as recited in claim 1, wherein said at least one $C_6+$ non-aromatic hydrocarbon is selected from the group consisting of cyclohexane, methylcyclopentane, 2-methylhexane, 3-methylhexane, 2,3-dimethylpentane, 2,4-dimethylpentane, dimethylcyclopentane, and mixtures thereof.

11. The process as recited in claim 1, wherein said at least one $C_6+$ non-aromatic hydrocarbon is present in said hydrocarbon composition feed in an amount from about 10 to about 50 percent by weight of said at least one $C_6+$ non-aromatic hydrocarbon having a boiling point within 10° C. at a pressure of about 101.3 kPa-a of the boiling point of benzene.

* * * * *